(12) United States Patent
Luk et al.

(10) Patent No.: US 7,129,351 B2
(45) Date of Patent: *Oct. 31, 2006

(54) PYRIMIDO COMPOUNDS HAVING ANTIPROLIFERATIVE ACTIVITY

(75) Inventors: Kin-Chun Luk, North Caldwell, NJ (US); Pamela Loreen Rossman, Nutley, NJ (US); Stefan Scheiblich, Penzberg (DE); Sung-Sau So, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 280 days.

This patent is subject to a terminal disclaimer.

(21) Appl. No.: 10/689,438

(22) Filed: Oct. 20, 2003

(65) Prior Publication Data

US 2004/0110773 A1 Jun. 10, 2004

Related U.S. Application Data

(60) Provisional application No. 60/423,670, filed on Nov. 4, 2002.

(51) Int. Cl.
C07D 487/04 (2006.01)
A61K 31/4985 (2006.01)
A61P 35/00 (2006.01)

(52) U.S. Cl. .................... 544/256; 514/262.1
(58) Field of Classification Search ........... 544/256; 514/262.1
See application file for complete search history.

(56) References Cited

U.S. PATENT DOCUMENTS

| | | | |
|---|---|---|---|
| 2,949,466 | A | 8/1960 | Hoefle et al. |
| 3,939,084 | A | 2/1976 | Sullivan |
| 4,425,346 | A | 1/1984 | Horlington |
| 4,886,807 | A | 12/1989 | Kitamura et al. |
| 6,150,373 | A | 11/2000 | Harris et al. |
| 6,451,804 | B1 | 9/2002 | Dunn et al. |
| 2004/0019210 | A1 | 1/2004 | Connolly et al. |
| 2004/0097485 | A1 | 5/2004 | Burkitt et al. |

FOREIGN PATENT DOCUMENTS

| | | |
|---|---|---|
| WO | WO 98/24432 | 6/1998 |
| WO | WO 99/61444 | 12/1999 |
| WO | WO 00 24744 | 5/2000 |
| WO | WO 01/29041 | 4/2001 |
| WO | WO 01/29042 | 4/2001 |
| WO | WO 01/64679 | 9/2001 |
| WO | WO 02/18380 A1 | 3/2002 |
| WO | WO 03/062236 | 7/2003 |

OTHER PUBLICATIONS

Draetta, G. and Pagano, M. in "Annual Reports in Medicinal Chemistry, vol. 31", 1996, Academic Press, San Diego, p. 241-246.*
Noble, M.E.M. et al, Science, vol. 303, 2004, pp. 1800-1805.*
Anderson, M.R. et al, Expert Opin. Investig. Drugs, 2003, 12(4) 577-592.*
Laird, A.D. et al, Expert Opin. Investig. Drugs, 2003, 12(1), 51-64.*
Traxler, Peter, Expert Opin. Ther. Targets, 2003, 7(2) 215-234.*
Sawyer, Tomi et al, Expert. Opin. Investig. Drugs, 2001, 10(7), 1327-1344.*
Sawyer, Tomi et al, Expert. Opin. Investig. Drugs, 2004, 13(1), 1-19.*
Anderson, M.R. et al, Expert Opin. Investig. Drugs, 2003, 12(4) 577-592.*
Laird, A.D. et al, Expert opin. Investig. Drugs, 2003, 12(1), 51-64.*
Traxler, Peter, Expert Opin. Ther. Targets, 2003, 7(2) 215-234.*
Hennequin L. F. et al., J. Med. Chem. 2002, vol. 45(6) pp. 1300-1312.
Klohs W. E. et al., Current Opinion in Biotechnology, 1999 vol. 10, pp. 544-549.
D. H. Boschelli & F. Boschelli, Drugs of the Future, 2000 25(7) pp. 717-736.
Ansel, H. et al., *Pharmaceutical Dosage Forms & Drug Delivery Systems* 6th Ed. 1995, p. 196.
J. Alexander, et al., *J. Med. Chem. 1988*, vol. 31, pp. 318-322.
Masquelin et al., *Helvetica Chimica Acta*, vol. 81 (1998) pp. 646-659.
Devi, et al., *Indian Journal of Heterocyclic Chemistry*, vol. 7, Jan.-Mar. 1998, pp. 193-196.
Tominaga et al., *Chemical & Pharmaceutical Bulletin*, vol. 32, No. 1, Jan. 1984, pp. 122-129.
Tominaga et al., *Heterocycles*, vol. 12, No. 4. 1979, pp. 503-504.
Marsh et al., *Chemical Communications*, 1996, pp. 1527-1528.
Z. Chem. 20 Jg (1980) Heft. 11, pp. 412-413.
Cappuccino et al., *Cancer Research*, vol. 24, Aug. 1964, pp. 1243-1248.
Chatterjee et al., *J. Sci. Industr. Res.*, vol. 17B, Feb. 1958, pp. 63-70.
Chatterjee et al., *J. Sci. Industr. Res.*, vol. 18B, Jul. 1959, pp. 272-278.
Graboyes et al., *Pteridines X.*, vol. 11 Jan. 6, 1968, pp. 568-573.
Grohe et al., *Liebigs Ann. Chem.*, 1974, pp. 2066-2073.
Gulevskaya et al., *Chemistry of Heterocyclic Compounds*, vol. 30, No. 9, 1994, pp. 1083-1091.
Hirota et al., *J. Chem. Soc. Perkin Trans. 1*, 1990, pp. 123-128.
Srivastava, et al., *Combinatorial Chemistry & High Throughout Screening*, 1999, 2, pp. 33-37.
Taylor et al., *Pyrimido [4,5-D]Pyrimidines*, vol. 82, pp. 5711-5718.
Wamhoff et al., *Heterocycles*, vol. 35, No. 2, 1993, pp. 1055-1066.
M. Hirota et al., "*A Facile Synthesis of 7-Substituted Pyrimido[4,5-d]-Pyrimidine-2,4-diones*", Synthesis, pp. 589-590 (1984).
Talpaz, M. et al., 2005 ASCO Annual Meeting: Abstract No. 6519, Leukemia, Lymphoma, Myeloma, and Transplantation (Adult), A Phase I Study of BMS-354825 in Patients with Imatinib-Resistant and Intolerant Chronic Phase Chronic Myeloid Leukemia (CML): Results from CA 180002.

* cited by examiner

*Primary Examiner*—Thomas C. McKenzie
(74) *Attorney, Agent, or Firm*—George W. Johnston; Patricia S. Rocha-Tramaloni

(57) ABSTRACT

Disclosed are novel pyrimido compounds that are inhibitors of Src family of tyrosine kinases. These compounds and their pharmaceutically acceptable salts are anti-proliferative agents useful in the treatment or control of solid tumors, in particular breast, colon, hepatic and pancreatic tumors. Also disclosed are pharmaceutical compositions containing these compounds and methods of treating cancer.

18 Claims, No Drawings

US 7,129,351 B2

PYRIMIDO COMPOUNDS HAVING ANTIPROLIFERATIVE ACTIVITY

PRIORITY TO RELATED APPLICATIONS

This application claims the benefit of Provisional Application Ser. No. 60/423,670, filed Nov. 4, 2002.

FIELD OF THE INVENTION

The present invention is directed to novel pyrimido compounds that inhibit the Src family of non-receptor tyrosine kinases (SFKs). These compounds and their pharmaceutically acceptable salts have antiproliferative activity and are useful in the treatment or control of cancer, in particular solid tumors. In addition these compounds have advantageous bioavailability profiles. This invention is also directed to pharmaceutical compositions containing such compounds and to methods of treating or controlling cancer, most particularly the treatment or control of breast, colon, hepatic and pancreatic tumors.

BACKGROUND OF THE INVENTION

Protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

Tyrosine kinases are a subset of protein kinases that catalyze the transfer of the terminal phosphate of adenosine triphosphate (ATP) to tyrosine residues on protein substrates. These kinases play an important part in the propagation of growth factor signal transduction that leads to cellular proliferation, differentiation and migration.

For example, the Src family of non-receptor tyrosine kinases has been specifically implicated in cancer cell modulation and growth. See D. H. Boschelli and F. Boschelli, "Small molecule inhibitors of Src family kinases," Drugs of the Future 2000, 25(7):717–736. Src over expression has been detected in colon, breast, hepatic and pancreatic tumors, as well as in certain B-cell leukemias and lymphomas. Id at 719. Increased Src expression and activity has also been shown to correlate with an increase in tumor malignancy. Id at 719. Thus, Src inhibitors can be useful as antitumor agents.

There are several examples of small molecule inhibitors of protein kinase catalytic activity. In particular, small molecule inhibitors typically block the phosphorylation of substrates by tightly interacting with the protein kinase ATP binding site (or "active site"). See WO 98/24432 and Hennequin L. F. et. al., J. Med. Chem. 2002, 45(6), pp1300. Several of these compounds inhibit multiple targets. For example, WO99/61444 (Warner-Lambert) discloses bicyclic pyrimidines and bicyclic 3,4-dihydropyrimidines of formula

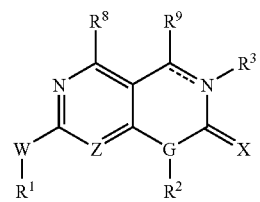

that are asserted to inhibit cyclin dependent kinases Cdk1, Cdk2 and Cdk4 as well as the growth factor receptor tyrosine kinase enzymes PDGFR and FGFR. Some compounds are also asserted to inhibit Cdk6.

U.S. Pat. No. 6,150,373 (Hoffmann-La Roche Inc.) discloses bicyclic nitrogen heterocycles of formula

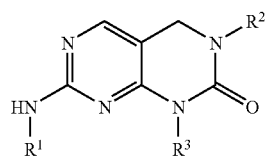

that are stated to inhibit the T-cell tyrosine kinase p56$^{lck}$.

WO 01/29041 A1 and WO 01/29042 (F. Hoffmann-La Roche AG) disclose alkylamino substituted bicyclic nitrogen heterocycles of formula

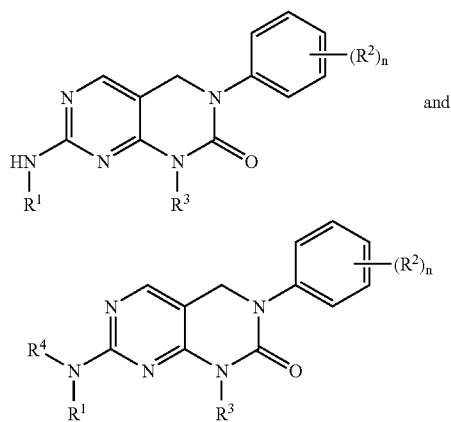

that are stated to inhibit p38 mediated cellular functions and are thus inhibitors of cellular proliferation.

WO 01/64679 A1 (SmithKline Beecham) discloses 1,5-disubstituted-3,4-dihydro-1H-pyrimido[4,5-D]pyrimidin-2-one compounds of formula

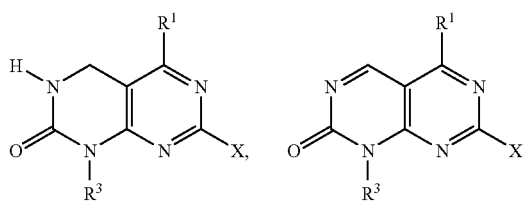

that are stated to be useful in treating CSBP/P38 kinase mediated diseases.

There continues to be a need for easily synthesized, small-molecule compounds effective in inhibiting the catalytic activity of protein kinases, in particular the Src family of non-receptor tyrosine kinases ("SFKs"), for treating one or more types of cancers, particularly solid tumors. It is preferable that such small molecule inhibitors also possess advantageous bioavailability profiles. It is thus an object of this invention to provide such compounds and pharmaceutical compositions containing these compounds.

SUMMARY OF THE INVENTION

The present invention relates to novel pyrimido compounds capable of inhibiting the activity of SFKs. These compounds are useful in the treatment or control of cancer, in particular the treatment or control of solid tumors. In particular this invention relates to compounds of formula

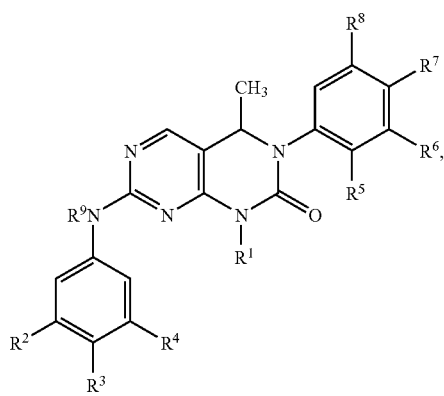

I or the pharmaceutically acceptable salts thereof, wherein $R^1$, $R^2$, $R^3$, $R^4$, $R^5$, $R^6$, $R^7$, $R^8$ and $R^9$ are as hereinafter defined.

The present invention also relates to pharmaceutical compositions comprising a therapeutically effective amount of one or more compounds of formula I and a pharmaceutically acceptable carrier or excipient.

The present invention further relates to a method for treating or controlling solid tumors, in particular treatment or control of breast, lung, colon and prostate tumors, most particularly breast or colon tumors, by administering to a human patient in need of such therapy an effective amount of a compound of formula I and/or a pharmaceutically acceptable salt thereof.

The present invention is further directed to novel intermediate compounds useful in the preparation of compounds of formula I.

DETAILED DESCRIPTION OF THE INVENTION

Definitions

As used herein, the following terms shall have the following definitions.

"Alkenyl" denotes a straight-chain or branched aliphatic hydrocarbon having at least one set of carbon-carbon double bond, for example vinyl, 2-butenyl, and 3-methyl-2-butenyl.

"Alkynyl" denotes a straight-chain or branched aliphatic hydrocarbon having at least one set of carbon-carbon triple bond, for example ethynyl, and 2-butynyl.

"Alkyl" denotes a straight-chain or branched saturated aliphatic hydrocarbon having 1 to 10, preferably 1 to 6, and more preferably 1 to 4 carbon atoms. Alkyl groups having 1 to 6 carbon atoms are also referred to herein as "lower alkyl." Typical lower alkyl groups include methyl, ethyl, propyl, isopropyl, butyl, t-butyl, 2-butyl, pentyl and hexyl. As used herein the sample designation $C_{1-4}$ alkyl means alkyl having from 1 to 4 carbon atoms.

"Alkoxy" means an alkyl radical that is attached to the remainder of the molecule by oxygen (RO—), e.g. methoxy, ethoxy.

"Aryl" means an aromatic carbocyclic radical, for example a 6–10 membered aromatic or partially aromatic ring system. Preferred aryl groups include, but are not limited to, phenyl, naphthyl, tolyl and xylyl.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective amount" or "Therapeutically Effective amount" means an amount of at least one compound for formula 1, or a pharmaceutically acceptable salt thereof, that significantly inhibits proliferation of tumor cells, including human tumor cell lines.

"Halogen" means fluorine, chlorine, bromine or iodine, preferably chlorine, fluorine or bromine.

"Hetero atom" means an atom selected from N, O and S, preferably N. If the hetero atom is N, it can be present as —NH— or —N-lower alkyl-. If the hetero atom is S, it can be present as S, SO or $SO_2$.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

"Heterocycle" or "heterocyclyl" means a 3- to 10-membered saturated or partially unsaturated non-aromatic monovalent cyclic radical having from one to 3 hetero atoms selected from nitrogen, oxygen or sulfur or a combination thereof. Examples of preferred heterocycles are piperidine, piperazine, pyrrolidine, and morpholine.

"Hydroxy" is a prefix indicating the presence of a monovalent OH group.

"$IC_{50}$" refers to the concentration of a particular compound according to the invention required to inhibit 50% of a specific measured activity. $IC_{50}$ can be measured, inter alia, as is described in Example 12, infra.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

In one embodiment, the invention relates to compounds of formula

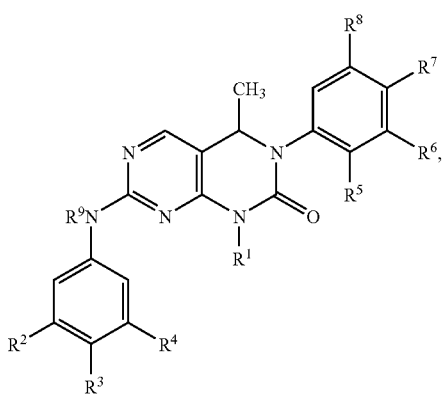

I or a pharmaceutically acceptable salt thereof, wherein
R$^1$ is selected from the group
H,
C$_{1-10}$ alkyl,
C$_{1-10}$ alkyl substituted by up to three groups selected from aryl, cycloalkyl, heteroaryl, heterocycle, NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$, wherein the aryl, cycloalkyl, heteroaryl, and heterocycle groups may each independently be substituted by up to three groups selected from NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$,
aryl,
aryl substituted by up to three groups selected from lower alkyl, NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$,
heteroaryl,
heteroaryl substituted by up to three groups selected from lower alkyl, R$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$,
heterocycle,
heterocycle substituted by up to three groups selected from lower alkyl, NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$,
C$_{3-10}$ cycloalkyl,
C$_{3-10}$ cycloalkyl substituted by up to three groups selected from lower alkyl NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$,
C$_{2-10}$ alkenyl,
C$_{2-10}$ alkenyl substituted by up to three groups selected from NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$, and
C$_{2-10}$ alkynyl, substituted by up to three groups selected from NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$;

R$^2$, R$^3$ and R$^4$ are independently selected from the group consisting of
H,
NR$^{10}$R$^{11}$,
OR$^{12}$,
SR$^{12}$,
C$_{1-10}$ alkyl,
C$_{1-10}$ alkyl substituted by up to three groups selected from cycloalkyl, heteroaryl, heterocycle, NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$; and wherein the cycloalkyl, heteroaryl, and heterocycle groups may each independently be substituted by up to three groups selected from lower alkyl, NR$^{10}$R$^{11}$, OR$^{12}$, SR$^{12}$, halogen, COR$^{113}$, CO$_2$R$^{13}$, CONR$^{13}$R$^{14}$, SO$_2$NR$^{13}$R$^{14}$, SOR$^{13}$, SO$_2$R$^{13}$, CN and NO$_2$,
heteroaryl, heteroaryl substituted by up to three groups selected from lower alkyl, NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$,
heterocycle, substituted by up to three groups selected from lower alkyl, NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$,
C$_{3-10}$ cycloalkyl,
C$_{3-10}$ cycloalkyl substituted by up to three groups selected from lower alkyl, NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$,
C$_{2-10}$ alkenyl,
C$_{2-10}$ alkenyl substituted by up to three groups selected from NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$,
C$_{2-10}$ alkynyl, and
C$_{2-10}$ alkynyl substituted by up to three groups selected from NR$^{10}$R$^{11}$, OR$^{12}$, SR$^{12}$, halogen, COR$^{13}$, CO$_2$R$^{13}$, CONR$^{13}$R$^{14}$, SO$_2$NR$^{13}$R$^{14}$, SOR$^{13}$, SO$_2$R$^{13}$, CN and NO$_2$ provided that at least one of R$^2$, R$^3$ or R$^4$ is not H;
R$^5$, R$^6$, R$^7$ and R$^8$ are independently selected from the group
H,
lower alkyl,
lower alkyl substituted by hydroxy or alkoxy,
NR$^{15}$R$^{16}$,
OH,
OR$^{17}$,
SR$^{17}$,
halogen,
COR$^{17}$,
CO$_2$R$^{17}$,
CONR$^{17}$R$^{18}$,
SO$_2$NR$^{17}$R$^{18}$,
SOR$^{17}$,
SO$_2$R$^{17}$, and
CN;

$R^9$ is selected from the group
H,

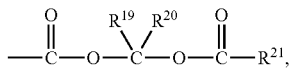

and
$COR^{17}$;
$R^{10}$ and $R^{11}$ are independently selected from the group
H,
$COR^{13}$,
$CO_2R^{13}$,
$CONR^{13}R^{14}$,
$SO_2R^{13}$,
$SO_2NR^{13}R^{14}$,
lower alkyl,
lower alkyl substituted by hydroxy, alkoxy or $NR^{15}R^{16}$,
cycloalkyl,
cycloalkyl substituted by hydroxy, alkoxy, lower alkyl, or $NR^{15}R^{16}$,
heterocycle, and
heterocycle substituted by hydroxy, alkoxy, lower alkyl, or $NR^{15}R^{16}$,
or, alternatively, $NR^{10}R^{11}$ can form a ring having 3 to 7 atoms, said ring optionally including one or more additional hetero atoms and being optionally substituted by the group consisting of one or more lower alkyl, $OR^{12}$, $COR^{13}$, $CO_2R^{13}$, $CONR^{13}R^{14}$, $SOR^{13}$, $SO_2R^{13}$, and $SO_2NR^{13}R^{14}$;
$R^{12}$ is selected from the group
H,
lower alkyl,
$COR^{13}$,
$CONR^{13}R^{14}$,
$C_{2-6}$ alkyl substituted by hydroxy, alkoxy, or $NR^{15}R^{16}$,
cycloalkyl,
cycloakyl substituted by hydroxy, alkoxy, lower alkyl, or $NR^{15}R^{16}$,
heterocycle, and
heterocycle substituted by hydroxy, alkoxy, lower alkyl, or $NR^{15}R^{16}$;
$R^{13}$ and $R^{14}$ are independently selected from the group
H,
lower alkyl,
$C_{2-6}$ alkyl substituted by hydroxy, alkoxy, or $NR^{15}R^{16}$,
cycloalkyl,
cycloalkyl substituted by hydroxy, alkoxy, lower alkyl, or $NR^{15}R^{16}$,
heterocycle, and
heterocycle substituted by hydroxy, alkoxy, lower alkyl, or $NR^{15}R^{16}$,
or, alternatively, $NR^{13}R^{14}$ can form a ring having 3 to 7 atoms, said ring optionally including one or more additional hetero atoms and being optionally substituted by the group consisting of one or more lower alkyl, $OR^{17}$, $COR^{17}$, $CO_2R^{17}$, $CONR^{17}R^{18}$, $SO_2R^{17}$, and $SO_2NR^{17}R^{18}$;
$R^{15}$ is selected from the group
H,
lower alkyl,
$COR^{17}$, and
$CO_2R^{17}$; and
$R^{16}$, $R^{17}$ and $R^{18}$ are independently selected from the group
H, and
lower alkyl,
or, alternatively, $NR^{15}R^{16}$ and $NR^{17}R^{18}$ can each independently form a ring having 3 to 7 atoms, said ring optionally including one or more additional hetero atoms;
$R^{19}$ and $R^{20}$ are independently selected from the group
H, and
lower alkyl; and
$R^{21}$ is selected from
lower alkyl, and
$C_{2-6}$ alkyl substituted by hydroxy, alkoxy or $NR^{15}R^{16}$, or a pharmaceutically acceptable salt thereof.

Compounds disclosed herein and covered by formula I above may exhibit tautomerism or structural isomerism. It is intended that the invention encompasses any tautomeric or structural isomeric form of these compounds, or mixtures of such forms (e.g. racemic mixtures), and is not limited to any one tautomeric or structural isomeric form depicted in formula I above.

When the compounds of formula I exhibit structural isomerism, the preferred optical isomer is depicted by formula Ia below

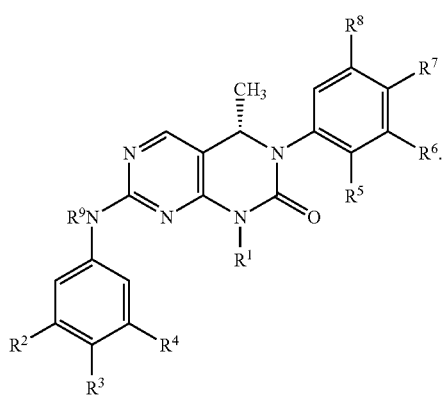

In a preferred embodiment, the invention relates to a compound of formula I wherein $R^1$ is selected from aryl, and aryl substituted by $OR^{12}$ or $CONR^{13}R^{14}$.

In another preferred embodiment of the compounds of formula I, $R^1$ is selected from lower alkyl and $C_{2-6}$ alkyl substituted by $OR^{12}$ or $CONR^{13}R^{14}$.

In another preferred embodiment of the compounds of formula I, $R^2$ and $R^3$ are each independently selected from alkyl and alkyl substituted by $OR^{12}$ or $NR^{10}R^{11}$.

In another preferred embodiment of the compounds of formula I, $R^5$, $R^6$ and $R^8$ are H and $R^7$ is O-lower alkyl, preferably O—$CH_3$.

In another preferred embodiment of the compounds of formula I, $R^5$ is halogen, preferably Br.

In another preferred embodiment of the compounds of formula I, $R^9$ is H.

The following compounds are preferred embodiments according to the present invention:
(±)-3-[7-[3-(2-Hydroxy-ethyl)-phenylamino]-3-(4-methoxy-phenyl)-4-methyl-2-oxo-3,4-dihydro-2H-pyrimido[4,5-d]pyrimidin-1-yl]-benzonitrile (Example 4);
(±)-3-[7-[3-(2-Diethylamino-ethyl)-phenylamino]-3-(4-methoxy-phenyl)-4-methyl-2-oxo-3,4-dihydro-2H-pyrimido[4,5-d]pyrimidin-1-yl]-benzonitrile (Example 5b);
(±)-3-[7-[3-(2-Dimethylamino-ethyl)-phenylamino]-3-(4-methoxy-phenyl)-4-methyl-2-oxo-3,4-dihydro-2H-pyrimido[4,5-d]pyrimidin-1-yl]-benzonitrile (Example 6);

(±)-3-(3-(4-Methoxy-phenyl)-4-methyl-7-{3-[2-(4-methyl-piperazin-1-yl)-ethyl]-phenylamino}-2-oxo-3,4-dihydro-2H-pyrimido[4,5-d]pyrimidin-1-yl)-benzonitrile (Example 7);

(±)-3-[7-[3-(2-Diethylamino-ethyl)-phenylamino]-3-(4-methoxy-phenyl)-4-methyl-2-oxo-3,4-dihydro-2H-pyrimido[4,5-d]pyrimidin-1-yl]-benzamide (Example 8);

(±)-3-[7-[3-(2-Dimethylamino-ethyl)-phenylamino]-3-(4-methoxy-phenyl)-4-methyl-2-oxo-3,4-dihydro-2H-pyrimido[4,5-d]pyrimidin-1-yl]-benzamide (Example 9);

(±)-3-(3-(4-Methoxy-phenyl)-4-methyl-7-{3-[2-(4-methyl-piperazin-1-yl)-ethyl]-phenylamino}-2-oxo-3,4-dihydro-2H-pyrimido[4,5-d]pyrimidin-1-yl)-benzamide (Example 10);

3-(2-Bromo-phenyl)-7-[4-(2-diethylamino-ethoxy)-phenylamino]-1,4-dimethyl-3,4-dihydro-1H-pyrimido[4,5-d]pyrimidin-2-one (enantiomer 1) Example 11f);

3-(2-Bromo-phenyl)-7-[4-(2-diethylamino-ethoxy)-phenylamino]-1,4-dimethyl-3,4-dihydro-1H-pyrimido[4,5-d]pyrimidin-2-one (enantiomer 2) Example 11g); and (±)-(3-(2-Bromo-phenyl)-7-[4-(2-diethylamino-ethoxy)-phenylamino]-1,4-dimethyl-3,4-dihydro-1H-pyrimido[4,5-d]pyrimidin-2-one.

The compounds of the invention inhibit Src tyrosine kinases. These compounds are useful in the treatment or control of cancer, in particular the treatment or control of solid tumors, specifically breast, colon, hepatic and pancreatic tumors. These compounds are highly permeable to cell membranes and thus possess advantageous bioavailability profiles such as improved oral bioavailability.

General Synthesis of Compounds According to the Invention

The compounds of the present invention can be prepared by any conventional means. Suitable processes for synthesizing these compounds are provided in the examples. Generally, compounds of formula I can be prepared according to the below described synthetic routes.

Scheme 1

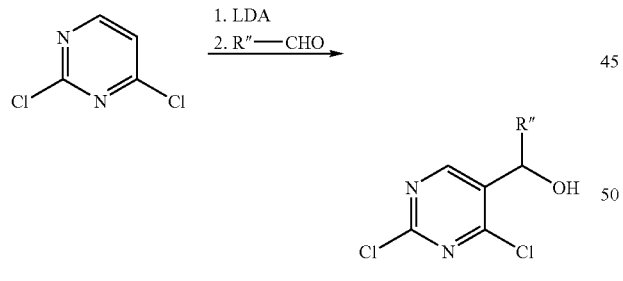

Scheme 2

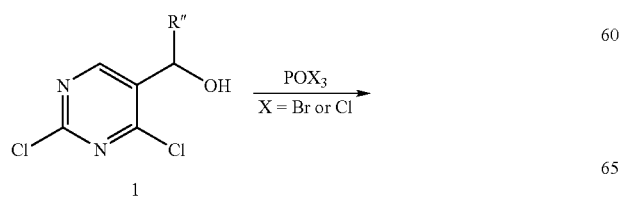

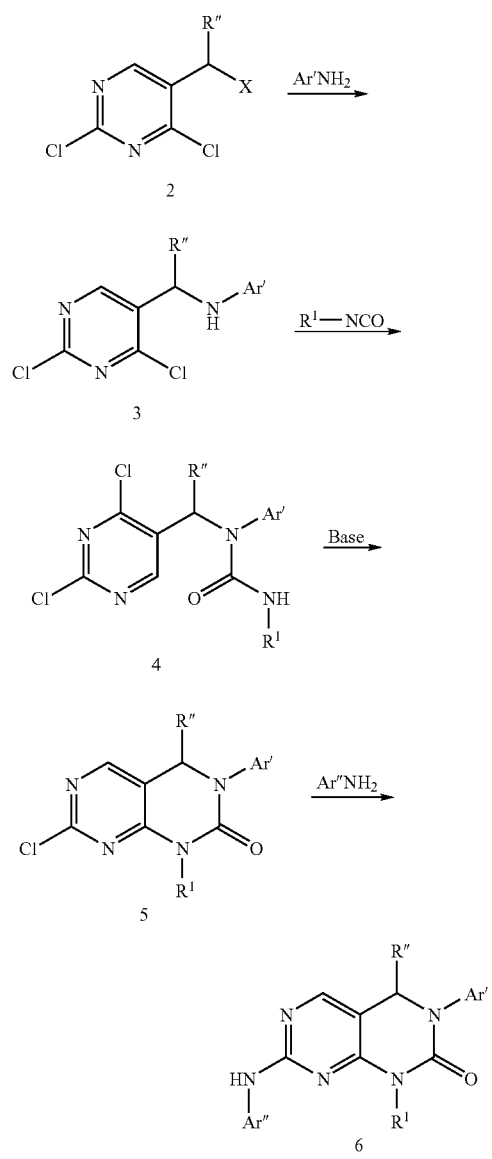

Scheme 3

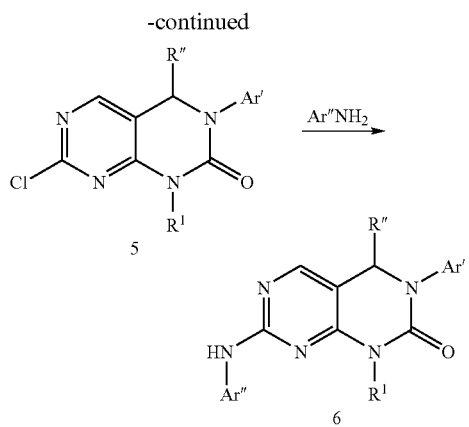

Scheme 4

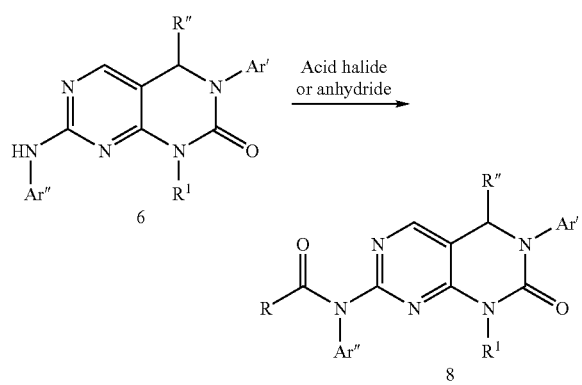

Scheme 5

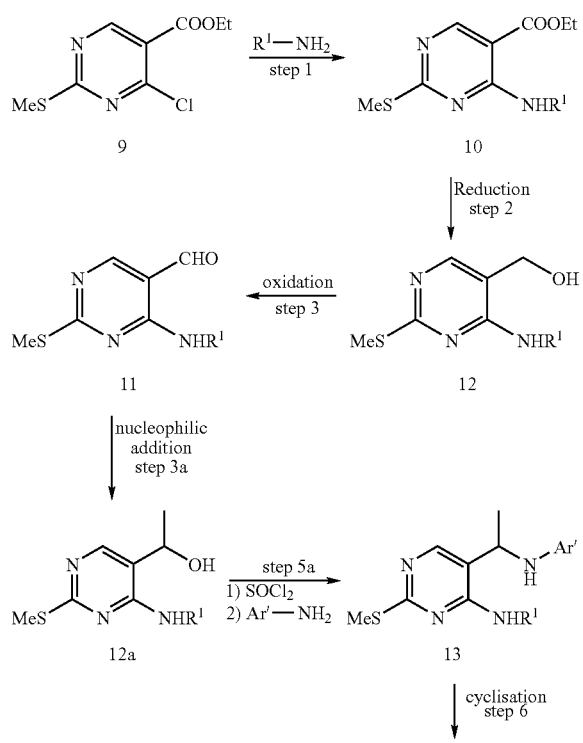

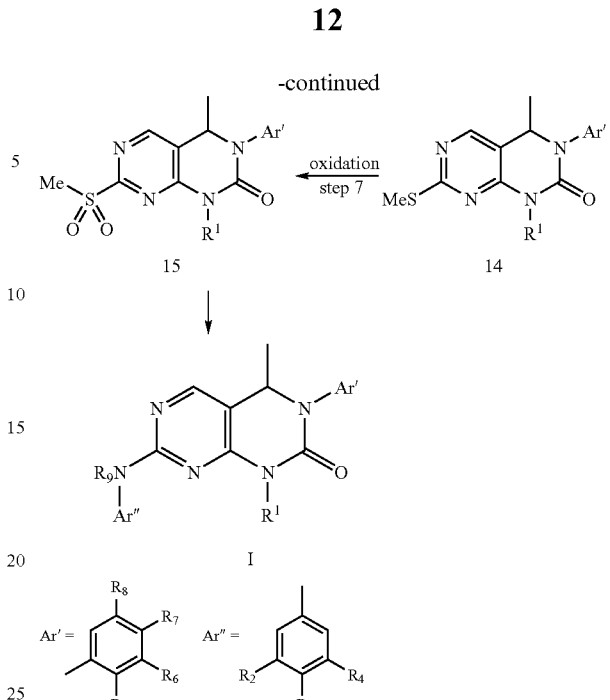

Compositions/Formulations

In an alternative embodiment, the present invention relates to pharmaceutical compositions comprising at least one compound of formula I, or a pharmaceutically acceptable salt or ester thereof.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, stearic acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention, including the compounds of formula I, are useful in the treatment or control of cell proliferative disorders, in particular oncological disorders. These compounds and formulations containing said compounds are particularly useful in the treatment or control of solid tumors, such as, for example, breast, colon, hepatic and pancreatic tumors. Thus, the present invention is further directed to a method for treating such solid tumors by administering to a patient in need of such therapy an effective amount of a compound of formula I and/or its salt.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The present invention is also directed to the following novel intermediates useful in the synthesis of compounds of formula I:

(±)-Acetic acid 2-{3-[8-(3-cyano-phenyl)-6-(4-methoxy-phenyl)-5-methyl-7-oxo-5,6,7,8-tetrahydro-pyrimido[4,5-d]pyrimidin-2-ylamino]-phenyl}-ethyl ester (Example 3c);

(±)-Methanesulfonic acid (2-{3-[8-(3-cyano-phenyl)-6-(4-methoxy-phenyl)-5-methyl-7-oxo-5,6,7,8-tetrahydro-pyrimido[4,5-d]pyrimidin-2-ylamino]-phenyl}-ethyl)-ester (Example 5a);

EXAMPLES

The following examples illustrate preferred methods for synthesizing the compounds and formulations of the present invention.

Example 1

Example 1a

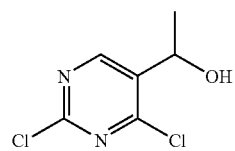

(±)-1-(2-4-Dichloro-pyrimidin-5-yl)-ethanol
193.03

(±)-1-(2,4-Dichloro-pyrimidin-5-yl)-ethanol was synthesized from 2,4-dichloropyrimidine (Aldrich) according to the literature procedure of Ple, N.; Turck, A.; Martin, P.; Barbey, S.; Queguiner, G. *Tet. Lett*, 1993 (34), 1605–1608.

Example 1b

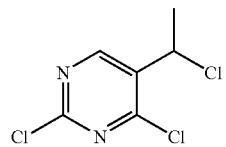

(±)-2,4-Dichloro-5-(1-chloroethyl)-pyrimidine
211.48

To a solution of (±)-1-(2,4-dichloro-pyrimidin-5-yl)-ethanol (1.27 g, 6.60 mmol) (from Example 1a supra) in phosphorus oxychloride (5.0 mL, 53.11 mmol) (Aldrich), at 0° C., was added diisopropylethyl-amine (2.60 mL, 14.78 mmol) (Aldrich). The reaction was stirred at 0° C. for 5 minutes, at ambient temperature for 15 minutes and then at 115° C. for 3 hours. The reaction was cooled to room temperature, diluted with toluene (10 mL) and the mixture was then poured into ice (15 g). After stirring for 10 minutes, the layers were separated and the aqueous extract was back washed with toluene. The combined organic extracts were dried over anhydrous sodium sulfate, filtered, and concentrated. Purification by flash chromatography (Biotage, 40M, 10:90 to 15:85 ethyl acetate-hexanes gradient) gave (±)-2,4-dichloro-5-(1-chloroethyl)-pyrimidine as an oil. (Yield 1.233 g; 88.3%).

Example 1c

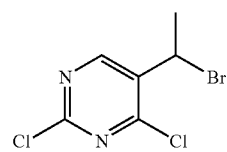

(±)-2,4-Dichloro-5-(1-bromoethyl)-pyrimidine
255.93

A solution of (±)-1-(2,4-dichloro-pyrimidin-5-yl)-ethanol (0.50 g; 2.60 mmol) (from Example 1a supra) and diisopropylethylamine (1.10 mL; 6.25 mmol) (Aldrich) in dibromomethane (0.35 mL) was cooled to 15° C. Phosphorus oxybromide (0.73 g; 2.83 mmol) was added in one portion. Cooling bath was removed and reaction mixture was stirred at room temperature. After 20 minutes, the reaction was diluted with ethyl acetate and water. The organic phase was washed with brine and then dried over anhydrous sodium sulfate, filtered and concentrated to give crude (±)-2,4-dichloro-5-(1-bromoethyl)-pyrimidine (0.61 g; 91.4%). Purification by flash chromatography (Biotage, 40M, 10:90 ethyl acetate-hexanes) gave pure (±)-2,4-dichloro-5-(1-bromoethyl)-pyrimidine as an oil which solidified when stored in refrigerator.

Alternatively (±)-2,4-dichloro-5-(1-bromoethyl)-pyrimidine was prepared as follows.

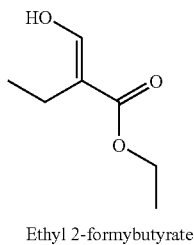

Ethyl 2-formylbutyrate

A solution of diisopropylamine (120.6 mL, 0.86 mol) (Aldrich) in tetrahyrofuran (370 mL) was cooled to −30° C. n-Butyllithium (2.5 M in hexanes, 344.2 mL, 0.86 mol) (Aldrich) was added drop wise at such a rate that the reaction mixture temperature was kept between −30 to 0° C. The reaction mixture was then cooled to −75° C. in a dry ice-acetone bath. A solution of ethyl butyrate (100 g, 0.86 mol) (Aldrich) in tetrahydrofuran (170 mL) was added drop wise over 28 minutes and keeping the reaction temperature between −75 to −70° C. The mixture was stirred at the same temperature for an additional 30 minutes. Ethyl formate (125 mL, 1.55 mol) (Aldrich) was then added to this mixture over 25 minutes and maintaining the temperature between −75 to −70° C. The resultant mixture was allowed to warm to room temperature and stirred at room temperature for 3 hours. With external cooling in a cold water bath to keep the reaction temperature below 30° C. acetic acid (98.55 mL, 1.72 mol) was added, followed by water (430 mL) and dichloromethane (200 mL). After separating the layers, the organic layer was washed with water (300 mL). The combined water layer was extracted with dichloromethane (200 mL). The combined organic layer was washed with aqueous sodium bicarbonate solution (200 mL). The basic aqueous solution was extracted with dichloromethane (100 mL). All organic layers were then combined, dried over sodium sulfate over night, filtered and distilled to remove solvent leaving about 180 mL. (Some of the product was distilled over with tetrahydrofuran.) The residue was distilled at 65–81° C. (23 mm Hg). The fraction distilling over at 70–81° C. (23 mm Hg) gave ethyl 2-formylbutyrate. (Yield 68.35 g, 55.1%).

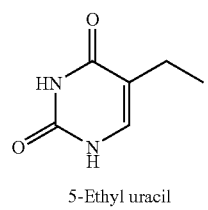

5-Ethyl uracil

Urea (19.39 g, 0.32 mol) (J. T. Baker) was added over 20 minutes to fuming sulfuric acid (26–29.5% free $SO_3$, 135 mL, 2.65 mol) (Aldrich) with cooling in an ice water bath maintaining the reaction temperature between 8 to 15° C. After stirring for an additional 30 minutes, ethyl 2-formylbutyrate (46.55 g, 0.32 mol) (from Example 1c, supra) was added over 18 minutes keeping the reaction at the same temperature. After stirring for another 30 minutes, a second portion of urea (15.07 g, 0.25 mol) was added over 10 minutes at the same temperature. The reaction mixture was then stirred at room temperature for 65 hours, and at 90–100° C. for 2 hours (gas evolution was observed, and reaction was exothermic, with reaction temperature rising to 110° C.). The mixture was cooled to 30° C. with an ice-water bath. Ice (270 g) was added slowly keeping the reaction below 35° C. The mixture was then cooled to 5° C. and stirred for 20 minutes. The solid formed was collected by filtration, washed with cold water, hexanes, and diethyl ether and dried by suction to give 5-ethyl uracil. (Yield 38.85 g, 85.9%).

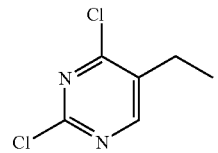

2,4-Dichloro-5-ethylpyrimidine

N,N-Diisopropylethylamine (195 mL, 0.86 mol) (Aldrich) was added slowly to a mixture of 5-ethyl uracil (52.3 g, 0.37 mol) (from Example 1c, supra) and phosphorous oxychloride (150 mL, 1.61 mol) (Aldrich) with external cooling in a cold water bath. The mixture was heated at reflux for 3.8 hours and cooled to room temperature. Mixture was then poured into ice (300 g). Ethyl acetate (100 mL) was added and mixture stirred at 20° C. for 30 minutes with cooling in an ice-water bath. The resulting mixture was filtered through Celite® and the filtrate extracted with ethyl acetate-hexanes (1:1, 3×300 mL). The combined organic layers was washed with water (250 mL), dried over sodium sulfate, filtered and concentrated to dryness. This residue was dissolved in ethyl acetate-hexanes (1:1) and filtered through TLC grade silica gel and eluting with the same solvent. The filtrate was concentrated to dryness to give 2,4-dichloro-5-ethyl-pyrimidine. (Yield 56.3 g, 85.2%).

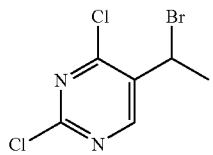

(±)-2,4-Dichloro-5-(1-bromoethyl)-pyrimidine

N-Bromosuccimimide (64.2 g, 0.35 mol) (Aldrich) and 2,2'-azo-bis-isobutyronitrile (AIBN, 1.78 g) (Aldrich) were added to a solution of 2,4-dichloro-5-ethylpyrimidine (56.3 g, 0.32 mol) (from Example 1c, supra) in carbon tetrachloride (400 mL). The mixture was heated at reflux for 1.5 hours and cooled to room temperature. Reaction mixture was filtered through TLC grade silica gel and eluted with ethyl acetate-hexanes (1:8). The filtrate was concentrated to dryness to give (±)-2,4-dichloro-5-(1-bromoethyl)-pyrimidine. (Yield 81.3 g, 100%).

Example 1d

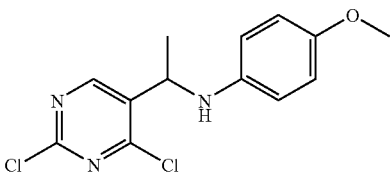

(±)-[1-(2,4-Dichloro-pyrimidin-5-yl)-ethyl]-(4-methoxy-phenyl)-amine
298.17

(±)-2,4-Dichloro-5-(1-bromoethyl)-pyrimidine (1.97 g; 7.70 mmol) (from Example 1c supra) was dissolved in acetonitrile (21 mL). p-Anisidine (0.95 g; 7.70 mmol) (Aldrich), potassium carbonate (1.17 g; 8.48 mmol) and potassium iodide (0.32 g; 1.93 mmol) were added and the mixture was stirred at room temperature. After 16 hours, the mixture was partitioned between ethyl acetate and water. The organic phase was washed with water and brine, dried over anhydrous sodium sulfate, filtered and concentrated. Purification by flash chromatography (Biotage 40M, 20:80 to 25:75 ethyl acetate-hexanes gradient) gave (±)-[1-(2,4-dichloro-pyrimidin-5-yl)-ethyl]-(4-methoxy-phenyl)-amine. (Yield 1.82 g; 76.3%).

Example 2

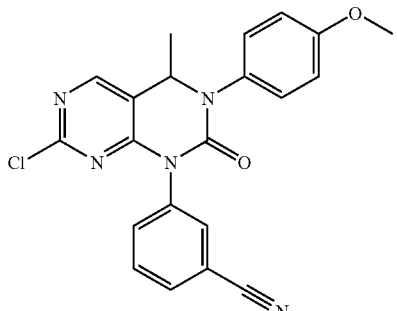

(±)-3-[7-Choro-3-(methoxy-phenyl)-4-methyl-2-oxo-3,4-dihydro-2H pyrimido[4,5-d]pyrimidin-1-yl]-benzonitrile
405.85

To a solution of (±)-[1-(2,4-dichloro-pyrimidin-5-yl)-ethyl]-(4-methoxy-phenyl)-amine (0.10 g; 0.34 mmol) (from Example 1d supra) in toluene (1 mL) was added 3-cyanophenyl isocyanate (66.6 mg; 0.46 mmol) (Aldrich). The mixture was heated in an oil bath at 110° C. for two hours. After cooling to room temperature, the reaction was concentrated under reduced pressure. The residue was triturated with hexanes and dried briefly. The solid residue (intermediate urea) was taken up in freshly distilled tetrahydrofuran (1.5 mL), cooled in an ice-brine bath and treated with potassium tert-butoxide (1.0 M in tetrahydrofuran; 370 µL; 0.37 mmol) (Aldrich). After 15 minutes in the cold the reaction was complete by TLC analysis and was filtered through a silica gel pad (0.5 g) and washed with ethyl acetate. The filtrate was concentrated and the residue was purified by flash chromatography (Biotage, 12M, 40:60 ethyl acetate-hexanes) to give (±)-3-[7-chloro-3-(4-methoxy-phenyl)-4-methyl-2-oxo-3,4-dihydro-2H-pyrimido[4,5-d]pyrimidin-1-yl]-benzonitrile as a solid. (Yield 0.13 g; 85.6%).

Example 3a

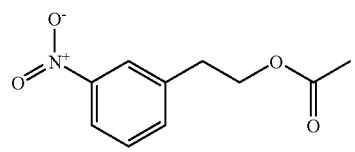

Acetic acid 2-(3-nitro-phenyl)-ethyl ester

3-Nitrophenethyl alcohol (55 g, 0.33 mol) (Aldrich) was dissolved in pyridine (1.2 L) (Aldrich). Acetic anhydride (215 mL, 2.14 mol) (Aldrich) was added slowly, and the mixture was stirred overnight at room temperature (TLC: 30% ethyl acetate in hexanes showed complete conversion). Ice and water (200 mL) were poured into the reaction mixture. The mixture was diluted with ethyl acetate, then successively washed with aqueous 1N hydrochloric acid (pH=~1), water, and brine. The organic layer was dried over anhydrous sodium sulfate, filtered, and concentrated under reduced pressure to give acetic acid 2-(3-nitro-phenyl)-ethyl ester as a yellow oil. (Yield 58.86 g, 0.28 mol, 85%).

Example 3b

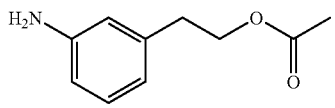

Acetic acid 2-(3-amino-phenyl)-ethyl ester

To a solution of acetic acid 2-(3-nitro-phenyl)-ethyl ester (15 g, 71.7 mmol) (from Example 3a supra) in ethyl acetate (150 mL), was added 10% palladium on carbon (1.5 g) (Aldrich). This mixture was hydrogenated at room temperature on the Parr apparatus at 50 psi for one hour. The reaction mixture was filtered over a bed of Celite® and washed with ethyl acetate. The filtrate was concentrated under reduced pressure to give acetic acid 2-(3-amino-phenyl)-ethyl ester. (Yield 12.81 g, 71.48 mmol, 99%).

Example 3c

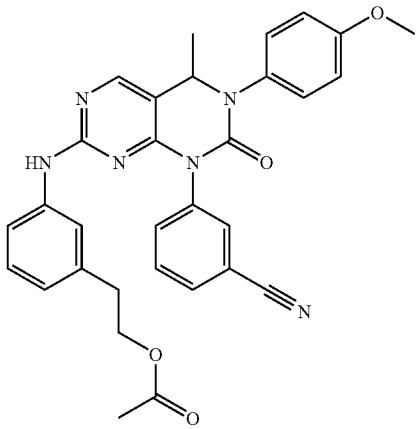

(±)-Acetic acid 2-{3-[8-(3-cyano-phenyl)-6-(4-methoxy-phenyl)-5-methoxy-7-oxo-5,6,7,8-tetrahydro-pyrimido[4,5-d]pyrimidin-2-ylamino]-phenyl}-ethyl ester 548.61

A mixture of (±)-3-[7-chloro-3-(4-methoxy-phenyl)-4-methyl-2-oxo-3,4-dihydro-2H-pyrimido[4,5-d]pyrimidin-1-yl]-benzonitrile (1.00 g; 2.42 mmol) (from Example 2 supra) and acetic acid 2-(3-amino-phenyl)-ethyl ester (2.03 g; 11.3 mmol) (from Example 3b supra) was heated in an oil bath at 110° C. for 1.5 hours. Upon cooling, the mixture was triturated with hexanes containing a small volume of ethyl acetate. The supernatant was decanted away and the residue was purified, in two runs, by flash chromatography (Biotage 40M; 50:50 to 70:30 ethyl acetate-hexanes gradient). The purified material was crystallized from ethyl acetate-hexanes to give (±)-acetic acid 2-{3-[8-(3-cyano-phenyl)-6-(4-methoxy-phenyl)-5-methyl-7-oxo-5,6,7,8-tetrahydro-pyrimido[4,5-d]pyrimidin-2-ylamino]-phenyl}-ethyl ester as a white solid. (1.03 g; 77.5%). Melting Point: 170–172° C.

Example 4

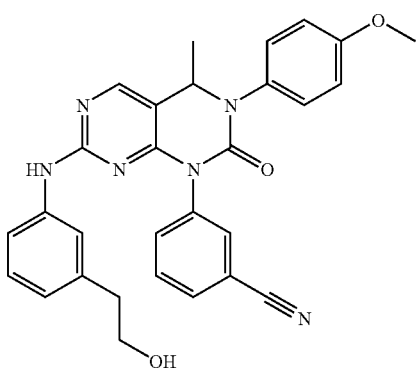

(±)-3-[7-[-3(2-Hyrdoxy-ethyl)-phenylamino]-3-(4-methoxy-phenyl)-4-methyl-2-oxo-3,4-dihydro-2H-pyrimido[4,5-d]pyrimidin-1-yl]-benzontrile 506.57

Acetic acid (±)-2-{3-[8-(3-cyano-phenyl)-6-(4-methoxy-phenyl)-5-methyl-7-oxo-5,6,7,8-tetrahydro-pyrimido[4,5-d]pyrimidin-2-ylamino]-phenyl}-ethyl ester (10 g; 1.81 mmol) (from Example 3c supra) was dissolved in a mixture of methanol (17 mL) and water (7 mL) and treated with potassium carbonate (1.00 g; 7.26 mmol) at room temperature for 19 hours. The reaction mixture was partitioned between ethyl acetate and water-brine mixture. The organic phase was washed with brine, dried over anhydrous sodium sulfate, filtered and concentrated. The crude material was purified by flash chromatography (Biotage 40M; ethyl acetate) to give (±)-3-[7-[3-(2-hydroxy-ethyl)-phenylamino]-3-(4-methoxy-phenyl)-4-methyl-2-oxo-3,4-dihydro-2H-pyrimido[4,5-d]pyrimidin-1-yl]-benzonitrile. (Yield 0.67 g; 72.9%). A small amount of additional material bumped over into the solvent trap during concentration. This material was recovered and crystallized from ethyl acetate. (Yield 0.09 g; 9.9%). Melting Point: 195–200° C. HR-MS (ES$^+$) m/z Calculated for $C_{29}H_{26}N_6O_3$ ([M+H]$^+$): 507.2139. Found: 507.2145. HR-MS(ES$^+$) m/z Calculated for $C_{29}H_{26}N_6O_3$ ([M+Na]$^+$): 529.9158. Found: 529.1963.

Example 5a

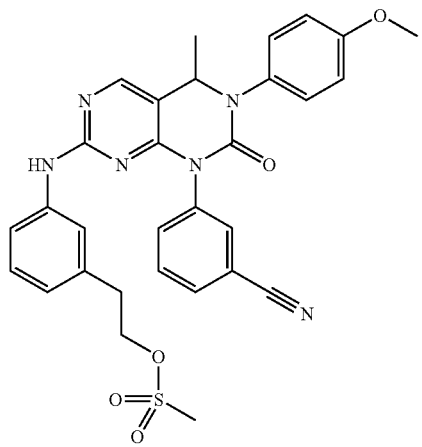

(±)-Methanesulfonic acid (2-{3-[8-(3-cyano-phenyl)-6-(4-methoxy-phenyl)-5-methyl-7-oxo-5,6,7,8-tetrahydro-pyrimido[4,5-d]pyrimidin-2-ylamino]-phenyl}-ethyl ester 584.66

(±)-3-[7-[3-(2-Hydroxy-ethyl)-phenylamino]-3-(4-methoxy-phenyl)-4-methyl-2-oxo-3,4-dihydro-2H-pyrimido[4,5-d]pyrimidin-1-yl]-benzonitrile (0.67 mg; 1.27 mmol) (from Example 4 supra) was suspended in dichloromethane (13 mL). The mixture was treated with triethylamine (0.23 mL; 1.65 mmol) and methane-sulfonyl chloride (0.13 mL; 1.68 mmol) (Aldrich). The solid went into solution as the methanesulfonyl chloride was added. After 45 minutes, the reaction was shown by thin layer chromatography to be complete. The reaction was diluted with additional dichloromethane and washed with water and then brine. The organic phase was dried over anhydrous sodium sulfate, concentrated and dried under high vacuum to give crude (±)-methanesulfonic acid (2-{3-[8-(3-cyano-phenyl)-6-(4-methoxy-phenyl)-5-methyl-7-oxo-5,6,7,8-tetrahydro-pyrimido[4,5-d]pyrimidin-2-ylamino]-phenyl}-ethyl)-ester as a foam. This material was used in the next step without further purification. (Yield: 0.76 g, 95.4%).

Example 5b

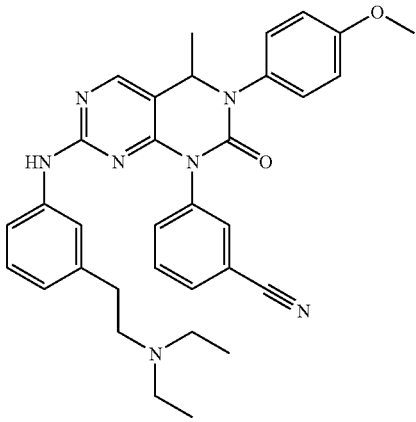

(±)-3-[7-[3-(2-Diethylamino-ethyl)-phenylamino]-3-(4-methoxy-phenyl)-4-methyl-2-oxo-3,4-dihydro-2H-pyrimido[4,5-d]pyrimidin-1-yl]-benzontrile 561.69

A mixture of (±)-methanesulfonic acid (2-{3-[8-(3-cyanophenyl)-6-(4-methoxy-phenyl)-5-methyl-7-oxo-5,6,7,8-tetrahydro-pyrimido[4,5-d]pyrimidin-2-ylamino]-phenyl}-ethyl)-ester (1.18 g; 2.02 mmol) (from Example 5a supra) and diethylamine (1.5 mL; 14.5 mmol) (Aldrich) in a pressure bottle and heated at 100° C. for 100 minutes. Upon cooling, the mixture was concentrated and the residue was partitioned between ethyl acetate and water. The organic phase was washed with brine, dried over anhydrous sodium sulfate and concentrated. Purification by flash chromatography (Biotage 40S; 100:0 to 50:50 ethyl acetate-methanol) followed by crystallization from ethyl acetate and hexanes gave (±)-3-[7-[3-(2-diethylamino-ethyl)-phenylamino]-3-(4-methoxy-phenyl)-4-methyl-2-oxo-3,4-dihydro-2H-pyrimido[4,5-d]pyrimidin-1-yl]-benzonitrile. (Yield 0.66 g; 57.9%).

Melting Point: 128–145° C. HR-MS(ES$^+$) m/z Calculated for $C_{33}H_{35}NO_7O_2$ ([M+H]$^+$): 562.2925. Found: 562.2925.

Example 6

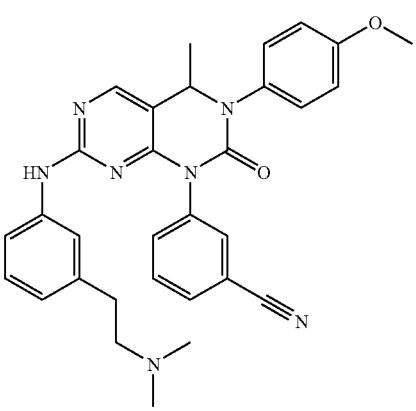

(±)-3-[7-[3-(2-Dimethylamino-ethyl)-phenylamino]-3-(4-methoxy-phenyl)-methyl-2-oxo-3,4-dihydro-2H-pyrimido[4,5-d]pyrimidin-1-yl]-benzonitrile 533.64

A mixture of (±)-methanesulfonic acid (2-{3-[8-(3-cyanophenyl)-6-(4-methoxy-phenyl)-5-methyl-7-oxo-5,6,7,8-tetrahydro-pyrimido[4,5-d]pyrimidin-2-ylamino]-phenyl}-ethyl)-ester (0.19 g; 0.32 mmol) (from Example 5a supra) and dimethylamine (2.0 M in tetrahydrofuran; 2.00 mL; 4.00 mmol) (Aldrich) in a bomb bottle and heated at 100° C. overnight. Upon cooling, the mixture was concentrated and the residue was partitioned between ethyl acetate and water. The organic phase was washed with water and brine, dried over anhydrous sodium sulfate and concentrated. At this point, the crude material was combined with material from an earlier run and purified by flash chromatography (Biotage, 12S; 100:0 to 50:50 ethyl acetate-methanol). This material was then crystallized from ethyl acetate and ether to give (±)-3-[7-[3-(2-dimethylamino-ethyl)-phenylamino]-3-(4-methoxy-phenyl)-4-methyl-2-oxo-3,4-dihydro-2H-pyrimido[4,5-d]pyrimidin-1-yl]-benzonitrile as a solid. (Yield 0.12 g; 26.8%).

Melting Point: 120–135° C. HR-MS(ES$^+$) m/z Calculated for $C_{31}H_{31}N_7O_2$ ([M+H]$^+$): 534.2612. Found: 534.2619.

Example 7

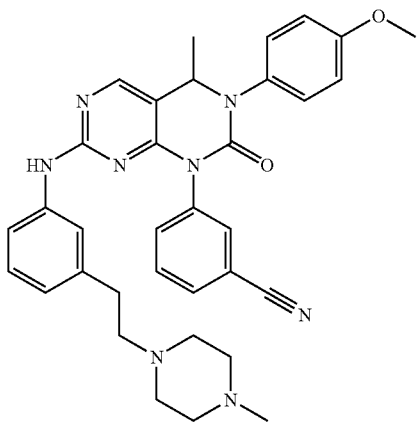

(±)-3-(3-(4-Methoxy-phenyl)-4-methyl-7-{3-[2-(4-methyl-piperazin-1-yl)-ethyl]-phenylamino}-2-oxo-3,4-dihydro-2H-pyrimido[4,5-d]pyrimidin-1-yl]-benzonitile 588.72

A mixture of (±)-methanesulfonic acid (2-{3-[8-(3-cyanophenyl)-6-(4-methoxy-phenyl)-5-methyl-7-oxo-5,6,7,8-tetrahydro-pyrimido[4,5-d]pyrimidin-2-ylamino]-phenyl}-ethyl)-ester (0.10 g; 0.16 mmol) (from Example 5a supra) and 1-methylpiperazine (0.25 mL; 2.23 mmol) (Aldrich) and heated at 110° C. for 1 hour. Upon cooling, the mixture was diluted with ethyl acetate and washed with water and brine. The organic phase was dried over anhydrous sodium sulfate, filtered, and concentrated. The crude material was purified by flash chromatography (Biotage 12S; 100:0 to 40:60 ethyl acetate-methanol gradient) and then crystallized from ethyl acetate-hexanes to give (±)-3-(3-(4-methoxy-phenyl)-4-methyl-7-{3-[2-(4-methyl-piperazin-1-yl)-ethyl]-phenylamino}-2-oxo-3,4-dihydro-2H-pyrimido[4,5-d]pyrimidin-1-yl)-benzonitrile. (Yield 60.6 mg; 64.1%).

Melting Point: 134–155° C. HR-MS(ES$^+$) m/z Calculated for $C_{34}H_{36}N_8O_2$ ([M+H]$^+$): 589.3034. Found: 589.3041.

Example 8

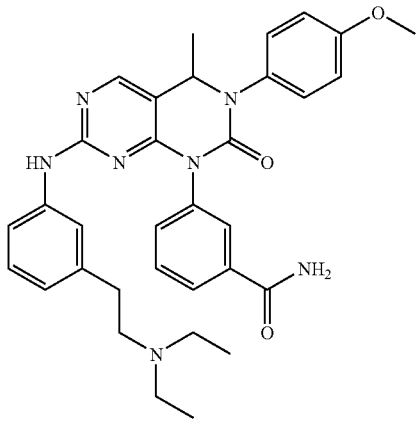

(±)-3-[7-[3-(2-Diethylamino-ethyl)-phenylamino]-3-(4-methoxy-phenyl)-
4-methyl-2-oxo-3,4-dihydro-2H-pyrimido[4,5-d]pyrimidin-1-yl]-benzamide 579.71

(±)-3-[7-[3-(2-Diethylamino-ethyl)-phenylamino]-3-(4-methoxy-phenyl)-4-methyl-2-oxo-3,4-dihydro-2H-pyrimido[4,5-d]pyrimidin-1-yl]-benzonitrile (0.35 g; 0.60 mmol) (from Example 5b supra) was dissolved in dimethyl sulfoxide (3.5 mL) and the resulting solution was cooled in an ice-water bath. Aqueous sodium hydroxide (1 M; 1.15 mL; 1.15 mmol) was added, resulting in the precipitation of the benzonitrile. Aqueous hydrogen peroxide (30%; 195 µL; 1.91 mmol) was then added. The benzonitrile slowly went back into solution. After 3 hours, water was added to the reaction mixture. The product initially separated out as a gum which then solidified. The solid was collected, washed with water and dried. Recrystallization from dichloromethane-ether gave (±)-3-[7-[3-(2-diethylamino-ethyl)-phenylamino]-3-(4-methoxy-phenyl)-4-methyl-2-oxo-3,4-dihydro-2H-pyrimido[4,5-d]pyrimidin-1-yl]-benzamide. (Yield 0.30 g; 84.8%).

Melting Point: 170–175° C. HR-MS(ES$^+$) m/z Calculated for $C_{33}H_{37}N_7O_3$ ([M+H]$^+$): 580.3031. Found: 580.3032. $IC_{50}$ 0.0045 µM.

Example 9

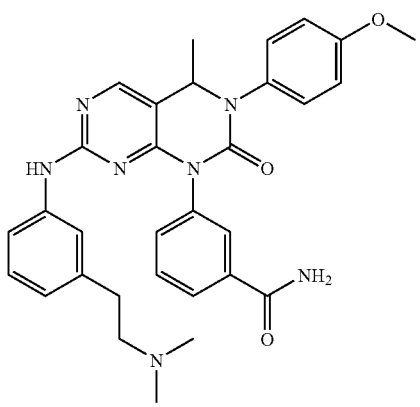

(±)-3-[7-[3-(2-Dimethylamino-ethyl)-phenylamino]-3-(4-methoxy-phenyl)-
4-methyl-2-oxo-3,4-dihydro-2H-pyrimido[4,5-d]pyrimidin-1-yl]-
benzamide 551.65

(±)-3-[7-[3-(2-Dimethylamino-ethyl)-phenylamino]-3-(4-methoxy-phenyl)-4-methyl-2-oxo-3,4-dihydro-2H-pyrimido[4,5-d]pyrimidin-1-yl]-benzonitrile (92.7 mg; 0.17 mmol) (from Example 6 supra) was dissolved in dimethyl sulfoxide (1.0 mL) and the resulting solution was cooled in an ice-water bath. Aqueous sodium hydroxide (1 M; 300 µL; 0.30 mmol) was added, resulting in the precipitation of the benzonitrile. Aqueous hydrogen peroxide (30%; 53 µL; 0.52 mmol) was then added. The benzonitrile went back into solution and the product then precipitate out of solution. After 4 hours, the reaction was diluted with water. The solid was collected, washed with water and dried. Recrystallization from dichloromethane-ether gave (±)-3-[7-[3-(2-dimethylamino-ethyl)-phenylamino]-3-(4-methoxy-phenyl)-4-methyl-2-oxo-3,4-dihydro-2H-pyrimido[4,5-d]pyrimidin-1-yl]-benzamide. (Yield 72.9 mg; 76.1%). Melting Point: 215–230° C. HR-MS(ES$^+$) m/z Calculated for $C_{31}H_{33}N_7O_3$ ([M+H]$^+$): 552.2718; Found: 552.2722.

Example 10

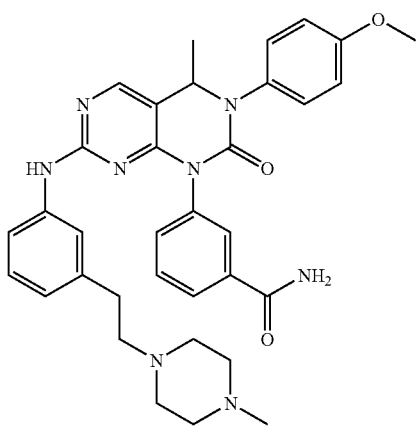

(±)-3-(3-(4-Methoxy-phenyl)-4-methyl-7-{3-[2-(4-methyl-piperazin-1-yl)-ethyl]-phenylamino}-2-oxo-3,4-dihydro-2H-pyrimido[4,5-d]pyrimidin-1-yl]-benzamide 606.73

(±)-3-(3-(4-Methoxy-phenyl)-4-methyl-7-{3-[2-(4-methyl-piperazin-1-yl)-ethyl]-phenylamino}-2-oxo-3,4-dihydro-2H-pyrimido[4,5-d]pyrimidin-1-yl)-benzonitrile (0.25 g; 0.41 mmol) (from Example 7 supra) was dissolved in dimethyl sulfoxide (2.5 mL) and the resulting solution was cooled in an ice-water bath. Aqueous sodium hydroxide (1 M; 750 µL; 0.75 mmol) was added, resulting in the precipitation of the benzonitrile. Aqueous hydrogen peroxide (30%; 130 µL; 1.27 mmol) was then added. The cooling bath was removed. The solid went back into solution and a new solid precipitated out. After 3 hours the reaction mixture was diluted with water. The solid was collected, washed with water and air-dried under the house vacuum. Purification by flash chromatography (Biotage 12S; 90:10 to 60:40 chloroform-methanol gradient) and then crystallization from methanol-ethyl acetate gave (±)-3-(3-(4-methoxy-phenyl)-4-methyl-7-{3-[2-(4-methyl-piperazin-1-yl)-ethyl]-phenylamino}-2-oxo-3,4-dihydro-2H-pyrimido[4,5-d]pyrimidin-1-yl)-benzamide as a white solid. (Yield 35.7 mg; 14.3%). A second crop was collected by addition of ether to the mother liquor. (Yield 87.8 mg; 35.1%). Melting Point: 243–251° C. HR-MS(ES$^+$) m/z Calculated for $C_{34}H_{38}N_8O_3$ ([M+H]$^+$): 607.3140; Found: 607.3144.

Example 11

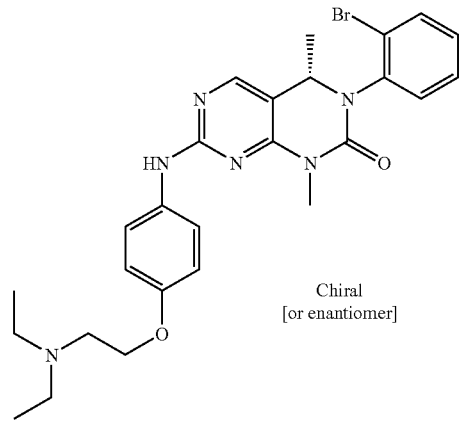

Chiral
[or enantiomer]

3-(2-Bromo-phenyl)-7-[4-(2-diethylamino-ethoxy)-phenylamino]-1,4-dimethyl-3,4-dihydro-1H-pyrimido[4,5-d]pyrimidin-2-one

Example 11a 1-(4-Methylamino-2-methylsulfanyl-pyrimidin-5-yl)-ethanol 1.5 g 4-Methylamino-2-methylsulfanyl-pyrimidine-5-carbaldehyde (prepared according to WO 00/24744) were dissolved in 30 mL THF. 14 mL of a 1.4 M solution of methyl magnesium bromide in ether were added drop-wise below 5° C. After stirring for 1 hr at 0° C., another 14 mL Grignard solution were added within 30 min. Stirring was continued for 30 min at 0° C. and finally at RT for 25 hrs. The mixture was quenched with saturated ammonium chloride solution and extracted with ethyl acetate.

Yield: 1.57 g of crude title product.

Example 11b

[5-(1-Chloro-ethyl)-2-methylsulfanyl-pyrimidin-4-yl]-methyl-amine 0.25 g of the product from Example 11a, supra, were dissolved in 10 mL chloroform and 0.30 g thionyl chloride were added drop-wise. The mixture was refluxed for 2 hrs and evaporated to yield 0.31 g of the title product as the hydrochloride salt.

Example 11c

5-[1-(2-Bromo-phenylamino)-ethyl]-2-methylsulfanyl-pyrimidin-4-yl-methyl-amine 0.25 g of the product from Example 11b, supra, and 34 mg sodium iodide in 10 mL acetonitrile were stirred for 15 min at RT. The resulting suspension was added drop-wise at RT to a mixture of 0.21 g 2-bromoaniline (Aldrich) and 0.33 g N-ethyl-di-isopropyl amine (Aldrich) in 5 mL acetonitrile. Stirring was continued for 16 hrs and the mixture was diluted with 20 mL water and extracted with dichloromethane. Chromatography on silica (eluent $CHCl_3$) yielded 158 mg of the title product.

Example 11d 3-(2-Bromo-phenyl)-1,4-dimethyl-7-methylsulfanyl-3,4-dihydro-1H-pyrimido[4,5-d]pyrimidin-2-one (enantiomers 1+2)

To 1.1 g of the product from Example 11c, supra, in 10 mL dry DMF were added 0.236 g sodium hydride (95%) with cooling. After stirring for 20 min at RT, the mixture was cooled to 5° C. and treated in small portions with a total of 1.01 g carbonyldiimidazole (Aldrich). Stirring was continued at 5° C. for 30 min and at RT over night. Excess sodium hydride was then destroyed by addition of a small amount of water under cooling. The mixture was diluted with water, extracted with ethyl acetate and the combined organic phases evaporated. The crude product was chromatographed on a chiral phase Chiracel OD-CSP (commercial 20 μm material from Daicel, eluent heptane/iso-propanol 1:1) to yield 470 mg each of the separated enantiomers of the title product as pale yellow powders. The first eluting enantiomer is termed "enantiomer 1", and likewise the corresponding enantiomer of the chiral compounds derived from it in the following preparation examples are termed "enantiomer 1". The second eluting enantiomer is termed "enantiomer 2", and likewise the corresponding enantiomer of the chiral compounds derived from it in the following preparation examples are termed "enantiomer 2".

Example 11e 3-(2-Bromo-phenyl)-7-methanesulfonyl-1,4-dimethyl-3,4-dihydro-1H-pyrimido[4,5-d]pyrimidin-2-one; enantiomer 1

0.628 g meta-chloroperbenzoic acid (77%) (Aldrich) were dissolved in 50 mL $CH_2Cl_2$ and this solution was dried by filtration over sodium sulfate. The dried MCPBA solution was added to a solution of 0.437 g of the enantiomer 1 from Example 11d, supra, in 20 mL $CH_2Cl_2$ dropwise at RT and stirring was continued over night. Excess peracid was destroyed by washing with dilute sodium bisulfite solution. The organic phase was washed with aqueous sodium bicarbonate, dried, and evaporated. Chromatography over silica in ethyl acetate/heptane yielded 430 mg of the title product.

Example 11f 3-(2-Bromo-phenyl)-7-[4-(2-diethylamino-ethoxy)-phenylamino]-1,4-dimethyl-3,4-dihydro-1H-pyrimido[4,5-d]pyrimidin-2-one (enantiomer 1)

152 mg of 4-(2-diethylamino-ethoxy)aniline (prepared accoridng to Rohamann, Friedrich, Chem. Ber. (1939) 72: p. 1333) in 1 mL dry NMP were treated with 0.43 mL of a 2M solution of HCl in ether and stirred at RT for 30 min. 100 mg of the product of Example 11e, supra, were added and the mixture was heated to 120–130° C. for 16 hrs. The mixture was diluted with 10 mL water and adjusted to alkaline pH by addition of NaOH. Extraction with CH₂Cl₂ and concentration of the organic phases gave a crude oil from which NMP and excess aniline were distilled off under high vacuum in the Kugelrohr oven. The residue was dissolved in 0.1 mL methanol and slowly diluted with 0.5 mL water. A fine precipitate formed, which was isolated by centrifugation and eventually purified further by preparative HPLC-MS.

Yield 20 mg of the title product.

Example 11q 3-(2-Bromo-phenyl)-7-[4-(2-diethylamino-ethoxy)-phenylamino]-1,4-dimethyl-3,4-dihydro-1H-pyrimido[4,5-d]pyrimidin-2-one (enantiomer 2)

The title product was obtained analogously to the compound of Example 11e and Example 11f, supra, but starting from enantiomer 2 of the product of Example 11d, supra.

Antiproliferative Activity

The antiproliferative activity of the compounds of the invention is demonstrated below in Example 12. These activities indicate that the compounds of the present invention are useful in treating cancer, in particular solid tumors such as breast, colon, hepatic and pancreatic tumors, more particularly breast and colon tumors.

Example 12

Kinase Assay

The activity of the compounds according to this invention as inhibitors for the src-family tyrosine kinases was shown by using the following assay.

SRC-Inhibitor-Assay Parameters:

| Reaction mixture: | |
|---|---|
| ATP | 5 µM |
| Peptide (Ro + Ja133-Ro): | 10 µM |
| Ja133-Ro | 196 nM |
| Ro | 9.8 µM |
| PT66 | 230 ng/mL |
| Assay buffer: | 4 mM MgCl₂ |
| | 2 mM TCEP |
| | 50 mM HEPES |
| | 0.1% Tween20 |
| | pH 7.3 |
| Enzyme: | 2.5 U/mL |
| Inhibitor: | max. 25 µM |
| | min. 0.42 nM |
| Materials: | |
| Eu-labelled phosphotyrosine antibody: | for Lck Cisbio Mab PT66-K, for Src EG & G Wallac PT66 Eu-W1024 (all commercially available). |

| -continued | |
|---|---|
| Peptides: | NH₂-A-E-E-E-I-Y-G-E-F-E-A-K-K-K-K-CONH₂, and Ja133-G-Aminocaprylic acid-A-E-E-E-I-Y-G-E-F-E-A-K-K-K-K-CONH₂, wherein Ja133 is LightCycler-Red 640-N-hydroxy succinimide ester ™; | whereby both peptides were synthesized by an optimized solid phase peptide synthesis protocol (Merrifield (1962) Fed. Proc. Fed. Amer. Soc Exp. Biol. 21, 412) on an Zinsser SMP350 peptide synthesizer. Shortly, the peptide was assembled on 160 mg (22.8 µmol scale) of a Rink-Linker modified polystyrene solid phase by repeatedly conjugating a twenty fold excess of aminoacids each protected by temporary piperidine labile Fmoc- and permanent acid labile tert-Bu-, BOC- and O-tert-Bu-groups depending on the side chain function. The substrate sequence AEEE-IYGEFEAKKKK was N-terminal additionally mounted with the spacer amino acids Aminocaprylic acid and Glycin. After cleavage of the N-terminal temporary protecting group the still attached and protected peptide was labeled with a 1.5 fold amount of LightCycler-Red 640-N-hydroxy succinimide ester (purchased from Roche Diagnostics GmbH) and triethylamine. After 3 hrs. the resin was washed with dimethylformamide and isopropanol until the eluates of the blue resin got colourless. The fully protected and labeled peptide was removed from the solid phase and released from the permanent protecting groups by treatment with a mixture of 80% trifluoracetic acid, 10% ethanedithiol, 5% thioanisol and 5% water. The substrate was finally isolated by a preparative reverse phase HPLC purification. The purification yielded 12.2 mg RP-HPLC single peak pure blue material (lyophilisate). The identity was proven by MALDI mass spectroscopy [2720.0].

Enzymes: Upstate Lck (p56$^{lck}$, active), Upstate Src (p60$^{c-src}$, partially purified) were purchased from UBI.

Homogenous, time-resolved Fluorescence Assay: Reader: Perkin Elmer, Wallac Viktor 1420-040 multilabel counter; Liquid handling system: Beckman Coulter, Biomek 2000.

ATP, Tween 20, HEPES were purchased from Roche Molecular Biochemicals, MgCl₂ and MnCl₂ were purchased from Merck Eurolab, TCEP was purchased from Pierce, 384 Well low volume fluorescence plates was purchased from Falcon.

Assay Description:

At first the enzyme is pre-incubated for 15 min. at 15° C. in aqueous solution with corresponding amounts of inhibitors according to this invention. Then the phosphorylation reaction is started by adding a reaction mixture, containing ATP, Peptide and PT66, and subsequent shaking. The proceeding of this reaction is immediately monitored using time resolved fluorescence spectroscopy in a suitable well plate reader.

The IC$_{50}$-values can be obtained from the reaction rates by using a non-linear curve fit (Excelfit).

The results of the foregoing in vitro experiments, including the IC$_{50}$ values, are set forth in Table 1 below. The compounds of the invention have IC$_{50}$ values in the above-reported assay of less than 1.0 µM.

TABLE 1

IC$_{50}$ (µM) - Enzyme Inhibition Assay

| Example | | Src |
|---|---|---|
| 4 | Racemic structure with HO-CH2CH2-phenyl-NH-, methoxyphenyl, and cyanophenyl substituents on pyrimidopyrimidinone core | <1.0 |
| 7 | Racemic structure with 4-methylpiperazinyl-ethyl-phenyl-NH-, methoxyphenyl, and cyanophenyl substituents | <1.0 |
| 6 | Racemic structure with dimethylamino-ethyl-phenyl-NH-, methoxyphenyl, and cyanophenyl substituents | <1.0 |
| 5b | Racemic structure with diethylamino-ethyl-phenyl-NH-, methoxyphenyl, and cyanophenyl substituents | <1.0 |

TABLE 1-continued
IC$_{50}$ (μM) - Enzyme Inhibition Assay
| Example | | Src |
|---|---|---|
| 8 | 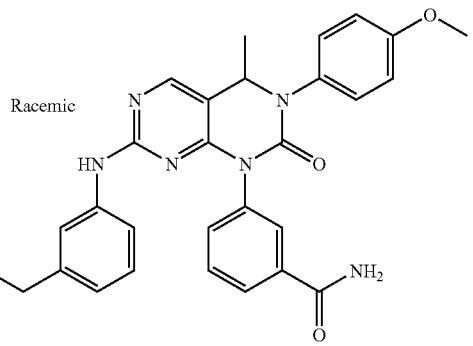 Racemic | <1.0 |
| 9 | 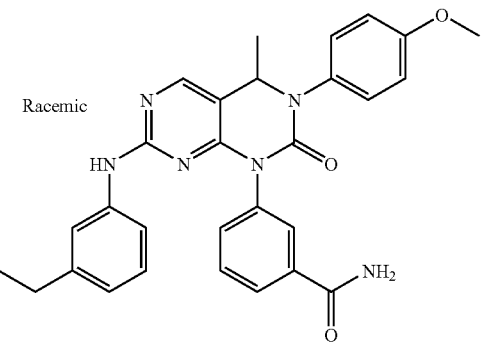 Racemic | <1.0 |
| 10 | 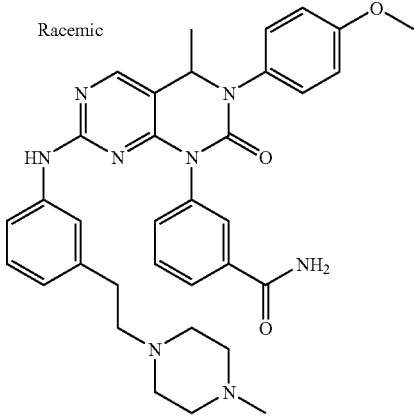 Racemic | <1.0 |

TABLE 1-continued

IC$_{50}$ (μM) - Enzyme Inhibition Assay

| Example | | Src |
|---|---|---|
| 11f (enantiomer 1) | 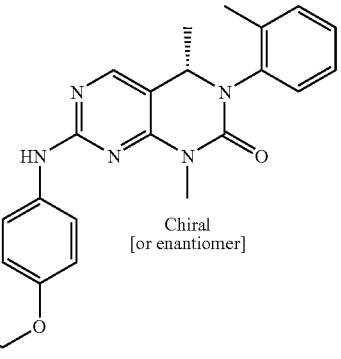 Chiral [or enantiomer] | <1.0 |

Example 13

Tablet Formulation

| Item | Ingredients | Mg/Tablet | | | | | |
|---|---|---|---|---|---|---|---|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound of the invention.

Manufacturing Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 14

Capsule Formulation

| Item | Ingredients | mg/Capsule | | | | |
|---|---|---|---|---|---|---|
| 1 | Compound A* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound A represents a compound of the invention.

Manufacturing Procedure:
1. Mix Items 1, 2 and 3 in a suitable mixer for 15 minutes.
2. Add Items 4 & 5 and mix for 3 minutes.
3. Fill into a suitable capsule.

Example 15

Injection Solution/Emulsion Preparation

| Item | Ingredient | mg/mL |
|---|---|---|
| 1 | Compound A* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound A represents a compound of the invention.

Manufacturing procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

Example 16

Injection Solution/Emulsion Preparation

| Item | Ingredient | mg/mL |
|---|---|---|
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:

1. A compound of formula:

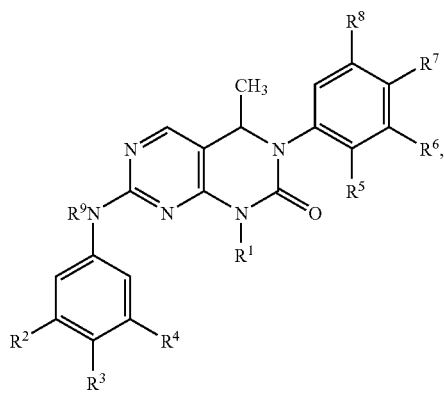

I or a pharmaceutically acceptable salt thereof, wherein
$R^1$ is selected from the group
H,
$C_{1-10}$ alkyl,
$C_{1-10}$ alkyl substituted by up to three groups selected from aryl, cycloalkyl, heteroaryl, heterocycle, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$, wherein the aryl, cycloalkyl, heteroaryl, and heterocycle groups may each independently be substituted by up to three groups selected from $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
aryl,
aryl substituted by up to three groups selected from lower alkyl, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
heteroaryl,
heteroaryl substituted by up to three groups selected from lower alkyl, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
heterocycle,
heterocycle substituted by up to three groups selected from lower alkyl, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
$C_{3-10}$ cycloalkyl,
$C_{3-10}$ cycloalkyl substituted by up to three groups selected from lower alkyl $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
$C_{2-10}$ alkenyl,
$C_{2-10}$ alkenyl substituted by up to three groups selected from $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$, and
$C_{2-10}$ alkynyl, substituted by up to three groups selected from $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$;
$R^2$, $R^3$ and $R^4$ are independently selected from the group consisting of
H,
$NR^{10}R^{11}$,
$OR^{12}$,
$SR^{12}$,
$C_{1-10}$ alkyl,
$C_{1-10}$ alkyl substituted by up to three groups selected from cycloalkyl, heteroaryl, heterocycle, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$; and wherein the cycloalkyl, heteroaryl, and heterocycle groups may each independently be substituted by up to three groups selected from lower alkyl, $NR^{10}R^{11}$, $OR^{12}$, $SR^{12}$, halogen, $COR^{113}$, $CO_2R^{13}$, $CONR^{13}R^{14}$, $SO_2NR^{13}R^{14}$, $SOR^{13}$, $SO_2R^{13}$, CN and $NO_2$,
heteroaryl, heteroaryl substituted by up to three groups selected from lower alkyl, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
heterocycle, substituted by up to three groups selected from lower alkyl, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
$C_{3-10}$ cycloalkyl,
$C_{3-10}$ cycloalkyl substituted by up to three groups selected from lower alkyl, $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
$C_{2-10}$ alkenyl,
$C_{2-10}$ alkenyl substituted by up to three groups selected from $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
$C_{2-10}$ alkynyl, and
$C_{2-10}$ alkynyl substituted by up to three groups selected from $NR^{10}R^{11}$, $OR^{12}$, $SR^{12}$, halogen, $COR^{13}$, $CO_2R^{13}$, $CONR^{13}R^{14}$, $SO_2NR^{13}R^{14}$, $SOR^{13}$, $SO_2R^{13}$, CN and $NO_2$,
Provided that at least one of $R^2$, $R^3$ or $R^4$ is not H,
$R^5$, $R^6$, $R^7$ and $R^8$ are independently selected from the group
H,
lower alkyl,
lower alkyl substituted by hydroxy or alkoxy,
$NR^{15}R^{16}$,
OH,
$OR^{17}$,
$SR^{17}$,
halogen,
$COR^{17}$,
$CO_2R^{17}$,
$CONR^{17}R^{18}$,
$SO_2NR^{17}R^{18}$,
$SOR^{17}$,
$SO_2R^{17}$, and
CN;

R⁹ is selected from the group
H,

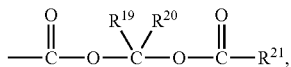

COR¹⁷;
R¹⁰ and R¹¹ are independently selected from the group
H,
COR¹³,
CO₂R¹³,
CONR¹³R¹⁴,
SO₂R¹³,
SO₂NR¹³R¹⁴,
lower alkyl,
lower alkyl substituted by hydroxy, alkoxy or NR¹⁵R¹⁶,
cycloalkyl,
cycloalkyl substituted by hydroxy, alkoxy, lower alkyl, or NR¹⁵R¹⁶,
heterocycle, and
heterocycle substituted by hydroxy, alkoxy, lower alkyl, or NR¹⁵R¹⁶,
or, alternatively, NR¹⁰R¹¹ can form a ring having 3 to 7 atoms, said ring optionally including one or more additional hetero atoms and being optionally substituted by the group consisting of one or more lower alkyl, OR¹², COR¹³, CO₂R¹³, CONR¹³R¹⁴, SOR¹³, SO₂R¹³, and SO₂NR¹³R¹⁴,
R¹² is selected from the group
H,
lower alkyl,
COR¹³,
CONR¹³R¹⁴,
C₂₋₆ alkyl substituted by hydroxy, alkoxy, or NR¹⁵R¹⁶,
cycloalkyl,
cycloakyl substituted by hydroxy, alkoxy, lower alkyl, or NR¹⁵R¹⁶,
heterocycle, and
heterocycle substituted by hydroxy, alkoxy, lower alkyl, or NR¹⁵R¹⁶;
R¹³ and R¹⁴ are independently selected from the group
H,
lower alkyl,
C₂₋₆ alkyl substituted by hydroxy, alkoxy, or NR¹⁵R¹⁶,
cycloalkyl,
cycloaklyl substituted by hydroxy, alkoxy, lower alkyl, or NR¹⁵R¹⁶,
heterocycle, and
heterocycle substituted by hydroxy, alkoxy, lower alkyl, or NR¹⁵R¹⁶,
or, alternatively, NR¹³R¹⁴ can form a ring having 3 to 7 atoms, said ring optionally including one or more additional hetero atoms and being optionally substituted by the group consisting of one or more lower alkyl, OR¹⁷, COR¹⁷, CO₂R¹⁷, CONR¹⁷R¹⁸, SO₂R¹⁷, and SO₂NR¹⁷R¹⁸;
R¹⁵ is selected from the group
H,
lower alkyl,
COR¹⁷, and
CO₂R¹⁷; and
R¹⁶, R¹⁷ and R¹⁸ are independently selected from the group
H, and
lower alkyl, or, alternatively, NR¹⁵R¹⁶ and NR¹⁷R¹⁸ can each independently form a ring having 3 to 7 atoms, said ring optionally including one or more additional hetero atoms;
R¹⁹ and R²⁰ are independently selected from the group
H, and
lower alkyl; and
R²¹ is selected from
lower alkyl, and
C₂₋₆ alkyl substituted by hydroxy, alkoxy or NR¹⁵R¹⁶,
or a pharmaceutically acceptable salt thereof.

2. The compound of claim 1 wherein R¹ is selected from aryl and aryl substituted by CN and CONR¹³R¹⁴.

3. The compound of claim 1 wherein R¹ is selected from lower alkyl.

4. The compound of claim 2 wherein R² is C₁₋₁₀ alkyl substituted by OR¹² or NR¹⁰R¹¹.

5. The compound of claim 3 wherein R² is OR¹².

6. The compound of claim 1 wherein R³ is H.

7. The compound of claim 1 wherein R³ and R⁴ are H.

8. The compound of claim 1 wherein R⁴ is C₁₋₁₀ alkyl substituted by NR¹⁰R¹¹.

9. The compound of claim 1 wherein R⁵ is halogen.

10. The compound of claim 1 having the formula

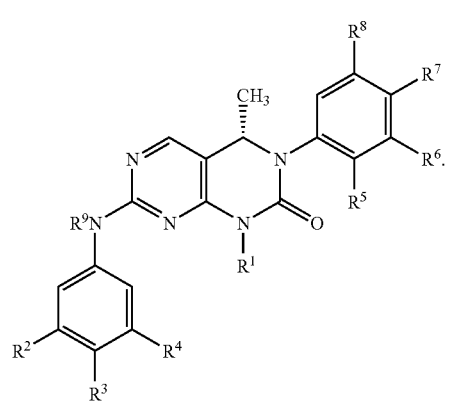

Ia

11. A compound selected from the group:
(±)-3-[7-[3-(2-Hydroxy-ethyl)-phenylamino]-3-(4-methoxy-phenyl)-4-methyl-2-oxo-3,4-dihydro-2H-pyrimido[4,5-d]pyrimidin-1-yl]-benzonitrile;
(±)-3-[7-[3-(2-Diethylamino-ethyl)-phenylamino]-3-(4-methoxy-phenyl)-4-methyl-2-oxo-3,4-dihydro-2H-pyrimido[4,5-d]pyrimidin-1-yl]-benzonitrile; and
(±)-3-[7-[3-(2-Dimethylamino-ethyl)-phenylamino]-3-(4-methoxy-phenyl)-4-methyl-2-oxo-3,4-dihydro-2H-pyrimido[4,5-d]pyrimidin-1-yl]-benzonitrile.

12. A compound selected from the group:
(±)-3-(3-(4-Methoxy-phenyl)-4-methyl-7-{3-[2-(4-methyl-piperazin-1-yl)-ethyl]-phenylamino}-2-oxo-3,4-dihydro-2H-pyrimido[4,5-d]pyrimidin-1-yl)-benzonitrile;
(±)-3-[7-[3-(2-Diethylamino-ethyl)-phenylamino]-3-(4-methoxy-phenyl)-4-methyl-2-oxo-3,4-dihydro-2H-pyrimido[4,5-d]pyrimidin-1-yl]-benzamide;
(±)-3-[7-[3-(2-Dimethylamino-ethyl)-phenylamino]-3-(4-methoxy-phenyl)-4-methyl-2-oxo-3,4-dihydro-2H-pyrimido[4,5-d]pyrimidin-1-yl]-benzamide; and (±)-3-(3-(4-Methoxy-phenyl)-4-methyl-7-{3-[2-(4-methyl-piperazin-1-yl)-ethyl]-phenylamino}-2-oxo-3,4-dihydro-2H-pyrimido[4,5-d]pyrimidin-1-yl)-benzamide.

13. The compound
(+)-3-(2-Bromo-phenyl)-7-[4-(2-diethylamino-ethoxy)-phenylamino]-1,4-dimethyl-3,4-dihydro-1H-pyrimido[4,5-d]pyrimidin-2-one.

14. The compound
(−)-3-(2-Bromo-phenyl)-7-[4-(2-diethylamino-ethoxy)-phenylamino]-1,4-dimethyl-3,4-dihydro-1H-pyrimido[4,5-d]pyrimidin-2-one.

15. The compound
(±)-3-(2-Bromo-phenyl)-7-[4-(2-diethylamino-ethoxy)-phenylamino]-1,4-dimethyl-3,4-dihydro-1H-pyrimido[4,5-d]pyrimidin-2-one.

16. A compound selected from the group:
(±)-Acetic acid 2-{3-[8-(3-cyano-phenyl)-6-(4-methoxy-phenyl)-5-methyl-7-oxo-5,6,7,8-tetrahydro-pyrimido[4,5-d]pyrimidin-2-ylamino]-phenyl}-ethyl ester and
(±)-Methanesulfonic acid (2-{3-[8-(3-cyano-phenyl)-6-(4-methoxy-phenyl)-5-methyl-7-oxo-5,6,7,8-tetrahydro-pyrimido[4,5-d]pyrimidin-2-ylamino]-phenyl}-ethyl)-ester.

17. A composition comprising a therapeutically effective amount of a compound of claim 1 and pharmaceutically acceptable carrier or excipient.

18. A method for treating breast or colon cancer comprising the administering of a therapeutically effective amount of a compound of claim 1.

* * * * *